United States Patent
Ruka et al.

[11] Patent Number: 5,021,304
[45] Date of Patent: Jun. 4, 1991

[54] MODIFIED CERMET FUEL ELECTRODES FOR SOLID OXIDE ELECTROCHEMICAL CELLS

[75] Inventors: Roswell J. Ruka, Churchill Boro; Charles J. Spengler, Murrysville, both of Pa.

[73] Assignee: Westinghouse Electric Corp., Pittsburgh, Pa.

[21] Appl. No.: 327,478

[22] Filed: Mar. 22, 1989

[51] Int. Cl.$^5$ .................... H01M 8/10; H01M 4/86
[52] U.S. Cl. .................... 429/30; 429/44; 427/115
[58] Field of Search ............. 429/30, 44; 427/115; 502/101

[56] References Cited
U.S. PATENT DOCUMENTS

| | | | |
|---|---|---|---|
| 4,582,766 | 4/1986 | Isenberg et al. | 429/30 |
| 4,702,971 | 10/1987 | Isenberg | 429/44 X |
| 4,767,518 | 8/1988 | Maskalick | 429/44 X |
| 4,847,172 | 7/1989 | Maskalick et al. | 429/30 |
| 4,849,254 | 7/1989 | Spengler et al. | 429/44 X |

*Primary Examiner*—Stephen J. Kalafut
*Attorney, Agent, or Firm*—Daniel P. Cillo

[57] ABSTRACT

An exterior porous electrode (10), bonded to a solid oxygen ion conducting electrolyte (13) which is in contact with an interior electrode (14), contains coarse metal particles (12) of nickel and/or cobalt, having diameters from 3 micrometers to 35 micrometers, where the coarse particles are coated with a separate, porous, multiphase layer (17) containing fine metal particles of nickel and/or cobalt (18), having diameters from 0.05 micrometers to 1.75 micrometers and conductive oxide (19) selected from cerium oxide, doped cerium oxide, strontium titanate, doped strontium titanate and mixtures thereof.

10 Claims, 2 Drawing Sheets

5,021,304

MODIFIED CERMET FUEL ELECTRODES FOR SOLID OXIDE ELECTROCHEMICAL CELLS

GOVERNMENT CONTRACT CLAUSE

The Government of the United States of America has rights in this invention pursuant to Contract No. DE-AC-2185-MC-22046, awarded by the United States Department of Energy.

BACKGROUND OF THE INVENTION

The use of a nickel-zirconia cermet fuel electrode for solid oxide electrolyte electrochemical cells is well known in the art, and taught, for example, in U.S. Pat. No. 4,490,444 (A. O. Isenberg). This electrode is approximately 50 micrometers thick, and contains nickel particles embedded in a zirconia skeletal structure. This fuel electrode or anode must be compatible in electrical, and physical-mechanical characteristics, such as thermal expansion, to the solid oxide electrolyte to which it is attached, and must be also be chemically resistant to contaminants, such as sulfur, found in contacting fuel feed gases. In U.S. Pat. No. 4,702,971 (A. O. Isenberg), an attempt was made to provide a sulfur resistant fuel electrode by coating the fuel electrode with an ionic-electronic conductive coating containing doped or undoped cerium oxide or doped or undoped uranium oxide, where the dopants were zirconia, thoria, or lanthanide oxides. The coatings were applied over "large", 1 micrometer to 5 micrometer conductor particles, in a zirconia skeleton, as salt solutions of the metal oxide coating desired. Such coatings solved sulfur tolerance problems, but even further improvements of the fuel electrodes are needed.

It is a main object of this invention to provide improved fuel electrodes for solid oxide electrolyte electrochemical cells.

SUMMARY OF THE INVENTION

Accordingly, the invention resides a composite of an exterior porous electrode bonded to a solid oxygen ion conducting electrolyte, where the electrolyte is also in contact with an interior electrode, the exterior electrode comprising coarse metal particles selected from the group consisting of nickel particles, cobalt particles, and mixtures thereof, having diameters from 3 micrometers to 35 micrometers, characterized in that the particles of the exterior electrode are coated with a separate, electronically conductive, porous, multiphase layer, consisting essentially of (a) fine metal particles selected from the group consisting of discrete nickel particles, discrete cobalt particles, and mixtures thereof, having diameters from 0.05 micrometer to 1.75 micrometer, and (b) conductive oxide selected from the group consisting of cerium oxide, doped cerium oxide, strontium titanate, doped strontium titanate, and mixtures thereof. In many embodiments, the coarse metal particles will be partly embedded in a skeletal structure comprising zirconia.

The invention also resides in a method of coating a separate, electronically conductive layer on an exterior, porous electrode bonded to a solid oxygen ion conducting electrolyte, where the electrolyte is also in contact with an interior electrode, characterized by the steps: (1) applying, to the exterior porous electrode, an admixture consisting essentially of: (a) a first metal containing salt where the metal containing component is selected from the group consisting of nickel, cobalt, and mixtures thereof, and the salt component is selected from the group consisting of nitrate, acetate, propionate, butyrate, and mixtures thereof, and (b) a second metal containing salt where the metal containing component is selected from the group consisting of cerium, doped cerium, strontium-titanium, doped strontium-titanium, and mixtures thereof, and the salt component is selected from the group consisting of nitrate, acetate, propionate, butyrate, and mixtures thereof and (c) non-ionic surfactant, and (2) heating the coating admixture in an atmosphere reducing to nickel, cobalt, and their mixtures, at a temperature effective to form a separate, solid, electronically conductive, porous, multiphase layer consisting essentially of conductive oxide selected from the group consisting of cerium oxide, doped cerium oxide, strontium titanate, doped strontium titanate, and mixtures thereof, containing therethrough fine metal particles selected from the group consisting of discrete nickel particles, discrete cobalt particles, and mixtures thereof, having diameters from 0.05 micrometer to 1.75 micrometers.

As a practical matter, the coarse metal particles in the exterior electrode will have diameters from 5 micrometers to 35 micrometers. Preferably, the fine metal particles in the electronically conductive, porous layer over the exterior electrode will have diameters from 0.25 micrometer to 0.75 micrometer. The porous conductor layer thickness is from 0.5 micrometer to 2.0 micrometers thick and will preferably be a complete covering. The term "doped" as used herein will mean "included in the chemical structure". Dopants may include alkaline earth materials, rare earth materials, yttrium, and aluminum.

BRIEF DESCRIPTION OF THE DRAWINGS

In order that the invention can be more clearly understood, convenient embodiments thereof will now be described, by way of example, with reference to the accompanying drawings in which.

DESCRIPTION OF THE PREFERRED EMBODIMENTS

Figure 1:
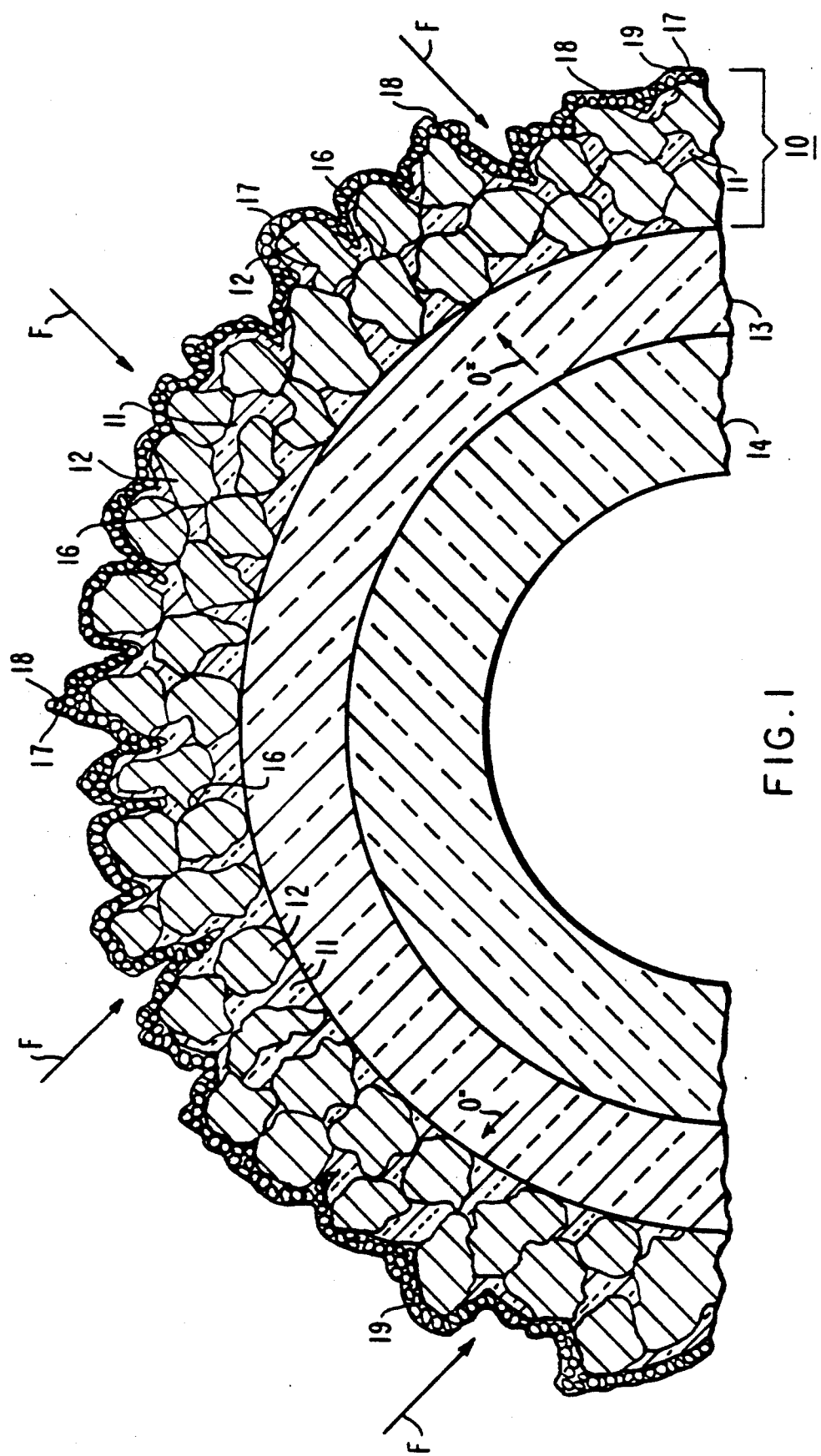
FIG. 1 is a composite, including a schematic end view in section showing one embodiment of a fuel electrode, having coarse metal particles partly embedded in an oxide skeleton structure, covered with the separate multiphase coating of this invention which contains small, discrete nickel and/or cobalt particles, in a ceramic oxide matrix, all disposed on top of an electrolyte.

Referring now to the Drawings, FIG. 1 is a much enlarged and detailed, idealized, schematic illustration of one embodiment of a composite electrochemical cell cross-section, showing exterior, porous fuel electrode structure 10, where a skeletal structure 11 embeds coarse metallic particles 12, to comprise the anode. A skeletal structure may not be necessary if the coarse metallic particles, for example nickel particles, can be sintered or otherwise bonded in place by appropriate means. This fuel electrode structure 10 contacts solid electrolyte 13 which is also in contact with the composite interior air electrode 14, to provide an electrochemical cell. The outer, multiphase layer of this invention is shown as coating 17.

The cell can have a variety of shapes but the preferred shape is tubular, as that configuration has already been used successfully in multi-kilowatt systems of solid oxide electrochemical cells. The electrolyte material 13 is typically an oxide having a fluorite-like crystal structure, but other simple oxides, mixed oxides, or mixtures of simple and mixed oxides can be used. The preferred electrolyte material is stabilized zirconia, a readily available commercial material. The zirconia may be stabilized, i.e., doped, with a number of elements, as is well known in the art, but rare earth element stabilized zirconia, specifically yttria stabilized zirconia, is preferred as it has excellent oxygen ion mobility, and a long history of operation in fuel or air environments. The electrolyte layer 13 is usually from 20 micrometers to 50 micrometers thick.

The interior air electrode 14, is preferably made of doped oxides or mixtures of oxides of the perovskite family, preferably $LaMnO_3$. Preferred dopants are Sr, Ca, Co, Ni, Fe, and Sn, where Sn and Ca can replace part of the La and the other dopants replace part of the Mn. The air electrode is usually from 50 micrometers to 1,000 micrometers thick. Thicknesses in the range of 600 micrometers to 1,000 micrometers are useful for self-supporting type air electrodes.

A preferred fuel electrode thickness is usually from 50 micrometers to 200 micrometers, though the thickness may be adjusted to the desired resistance of the cell. Nickel and/or cobalt particles 12 are used in the porous fuel electrode structure 10. The particles 12, which are from 3 micrometers to 35 micrometers in diameter, may be applied to contact the electrolyte as a powder layer in many different ways, including slurry dipping and spraying. Another method of application is a tape transfer technique, which is useful because of ease of mass fabrication, registering of dimensions, and uniformity in thickness and porosity. Particles less than 3 micrometers are extremely difficult to effectively apply by most fabrication techniques. The preferred particle size is from 5 micrometers to 35 micrometers.

A skeletal material 11 can be used to bind the coarse conductor particles 12 to the electrolyte 13, and provide a matrix partly embedding the coarse conductor particles. The skeletal material can be applied by vapor deposition and formed from two reactants. The first reactant can be water vapor, carbon dioxide or oxygen itself, and the second reactant can be a metal halide, preferably zirconium tetrachloride, plus the halide of a stabilizing element, such as yttrium chloride. The skeletal binding material 11 may be selected to be the same material as the electrolyte (or the same material modified by doping) so that a good bond forms between the binding material 11 and the electrolyte 13 and there is a good thermal match between the two materials. A useful skeletal binding material is yttria stabilized zirconia although a wide variety of ceramic metal oxides that are compatible with the electrolyte can be used.

Electrochemically active sites in solid state electrochemical cells are where the reactant, electrolyte and electrode interface. In the case of FIG. 1, these electrochemically active sites are where the fuel gas, F, shown by an arrow, is capable of combining with oxygen ions $O^=$ shown by the the arrow passing through electrolyte layer 13, and where electron transfers can take place to generate an electric current. By using coarse particles and an embedding skeleton alone, the number of active areas 16 would be rather limited.

FIG. 1 also shows how the nickel and/or cobalt particles 12 are covered, preferably completely, with an electronically conductive, porous, outer coating 17. Within the electronically conductive, porous, outer coating 17 are discrete, fine, nickel and/or cobalt particulate precipitates 18, much smaller than the coarse particles 12. The coating 17 can be applied by any means, although simple impregnation of the fuel electrode 10 from an aqueous salt solution is preferred.

As can be seen in FIG. 1, where, as a non-limiting illustration, the relative dimensions of the layers are scaled to a 50 micrometer thick air electrode 14, a 20 micrometer thick electrolyte 13, a 50 micrometer thick fuel electrode 10 containing coarse metal particles of from about 20 micrometer to 35 micrometer approximate diameter, and a 1 micrometer to 2 micrometer thick electronically conductive, outer coating 17 containing discrete, fine nickel and/or cobalt particles 18, about 0.5 micrometer in diameter. The fine particles 18 are primarily in the form of a fine precipitate, generally isolated by an oxide matrix 19, preferably surrounding and encapsulating the particles 18, so that said particles will not agglomerate or sinter together into large lumps upon heating or operation in an electrochemical environment. The metal particle phase is an essential component of the outer coating 17.

This multiphase coating 17 not only vastly increases the number of electrochemically active sites over the case where coarse particles are used alone, but also improves the catalytic activity of the fuel electrode. Most of the fine particles 18 do not contact each other or the coarse metal particles 12 found deep within the fuel electrode. The fine particles 18 have diameters from 0.05 micrometer to 1.75 micrometers, preferably from 0.25 micrometers to 0.75 micrometers. Sizes over 1.75 micrometers would reduce overall active chemical site surface area, eliminating the main advantage of the coating of this invention. While not clearly shown in FIG. 1, the multiphase outer coating 17 can extend deeply into interstices deep within the fuel electrode structure.

Useful, conductive, ceramic oxides for the matrix 19 of the multiphase outer coating 17, are selected from the group consisting of cerium oxide, doped cerium oxide, strontium titanate ($SrTiO_3$), doped strontium titanate, and mixtures thereof, preferably cerium oxide or doped cerium oxide. Useful dopant oxides, included in a "minor amount"; i.e., up to about 45 mole % doping element, for the purpose of increasing electronic conduction or causing a closer match of the coefficient of thermal expansion, are selected from the group consisting of oxides of: alkaline earth metal materials Mg, Ca, Sr, Ba; rare earth materials La, Ce, Pr, Nd, Sm, Eu, Gd, Tb, Dy, Ho, Er, Tm, Yb; Y; and Al; and mixtures of all these. Cerium can be used when strontium titanate is to be doped and strontium can be used when cerium is to be doped. Preferred dopants are oxides of Ca and Sm.

Figure 2:
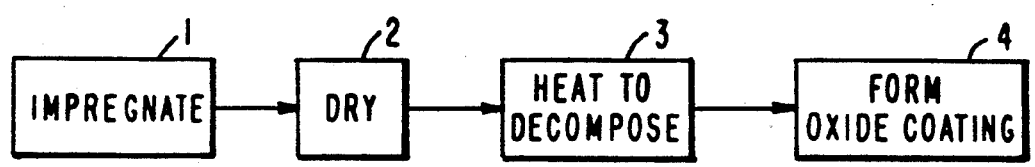
FIG. 2 is a block diagram showing the method of this invention.

In one method of coating, the coarse metal particle embedded electrode is impregnated, step 1 of FIG. 2, with a metal salt solution, containing nickel and/or cobalt salts plus matrix material salts, that, when dried, step 2 in FIG. 2, and then heated over about 500° C., step 3 in FIG. 2, decomposes or reacts to form the desired mixed oxide coating, step 4 in FIG. 2. Useful salts are selected from the group consisting of nitrate, acetate, propionate, butyrate, and mixtures thereof.

Preferably, nitrate is not used alone, since it causes difficulty some times in forming uniform films. The preferred salts are acetate alone or acetate plus nitrate. For example, an aqueous mixed solution of nickel nitrate, cerium acetate, and a minor amount of samarium acetate can be used.

The impregnated salt solution will also contain an amount of non-ionic surfactant, i.e., surface active agent, effective to allow wetting of the fuel electrode surface to which it is to be applied. Use of surfactant allows better penetration and more uniform coating of the anode cermet surface. The preferred range of surfactant addition is from approximately 0.5 wt. % to 6 wt. % of salt solution weight. These materials are well known in the art and can include alkylaryl ether alcohols, alkylaryl polyether alcohols, alkylaryl polyethylene glycol ethers, and the like. The surfactant is generally eliminated by vaporization or decomposition during heating to form the multiphase layer. These materials help the impregnating solution wet the pore surfaces of the fuel electrode materials.

A minor, optional amount of a colloidal solution of hydrated alumina or zirconia can also be added to the metal oxide precursor salt solution to help reduce cracking or spalling of the film coating. Before impregnation, the metal oxide precursor salt solution is de-aerated to remove trapped air, by a process such as boiling for a short period. The solution can be an aqueous solution or an organic based solution, for example a methanol solution of the salts.

Preferably, the metal salt solution mixture, is applied by vacuum impregnation techniques, where the cell is pretreated by being placed in a container and drawing a vacuum. Then, the de-aerated metal oxide precursor salt solution is added to the container until the fuel electrode of the cell is covered. This procedure ensures complete penetration of solution through the bulk of the fuel electrode. Alternative but less preferred application techniques are pressurized spraying and dipping. After impregnation, the metal containing material is allowed to dry, preferably at approximately 25° C. It may then be reimpregnated or coated if desired and again dried, to form, preferably, a continuous layer on and within the fuel electrode.

When the solution dries, the salt is heated up in an atmosphere of hydrogen and water, containing a little more hydrogen than just needed to decompose the salt to elemental nickel and/or cobalt and form an oxide of the other metal components contained in the solution. In the case of nickel nitrate, cerium acetate, and a minor amount of samarium acetate, this decomposition heating will form fine, elemental Ni precipitate particles, and samarium doped cerium oxide. This elemental metal plus matrix oxide will coat the surfaces of the cermet particles in the porous electrode.

The impregnated cell should be heated slowly, for example at 50° C. to 100° C./hour, up to about 600° C., to reduce the tendency of the films of the impregnated materials to crack or spall. The cells containing the impregnated cermet electrodes can then be assembled into a cell bundle, placed into a generator, and heated to the 1,000° C. operating temperature of the generator and operated.

The invention will now be illustrated with reference to the following example.

EXAMPLE

A tubular cell, closed at one end was prepared. It was approximately 400 mm long and 13 mm in diameter, consisting of a 2 mm thick porous support tube of calcia stabilized zirconia, 1 mm thick 40% porous air electrode of doped lanthanum manganite on top of the support tube, and a 50 micrometer thick electrolyte of yttria stabilized zirconia $(ZrO_2)_{0.90}(Y_2O_3)_{0.10}$ on the air electrode. A 100 micrometer thick layer of nickel powder, about 20 micrometers to 35 micrometers in diameter, was deposited over the electrolyte by means of slurry dipping. A ceramic skeleton of yttria stabilized zirconia was deposited around the nickel powder layer to physically attach it to the electrolyte, providing a cermet consisting of nickel and reinforcing zirconia ceramic.

A mixed salt impregnating solution was prepared and consisted of 0.0077 mole cerium acetate; 0.0023 mole samarium nitrate; 0.01 mole nickel nitrate; 0.3 cubic centimeter of non-ionic surfactant; 20 cubic centimeters of water; and 3 cubic centimeters of a 2% colloidial solution of hydrated alumina. The solution was applied to the nickel-zirconia cermet fuel electrode surface by brushing. The impregnated electrode was then dried in a hood at room temperature.

The impregnated, mixed salts were thermally decomposed to a mixed oxide during a heat-up procedure for testing the cell. Heating was at a slow rate up to a temperature of 1,000° C. The resulting electronically conductive, porous, multiphase layer over and within the cermet fuel electrode was a mixture of nickel particles and samarium doped cerium oxide plus alumina, i.e., $Ni + Ce_{0.75}Sm_{0.25}O_{1.875} + Al_2O_3$. Microscopic examination of electrodes after operation and testing showed that the impregnation was embedded in the voids of the porous nickel-zirconia cermet electrode, and the diameters of discrete nickel particle precipitates were from 0.4 micrometer to 1.70 micrometers.

Figure 3:
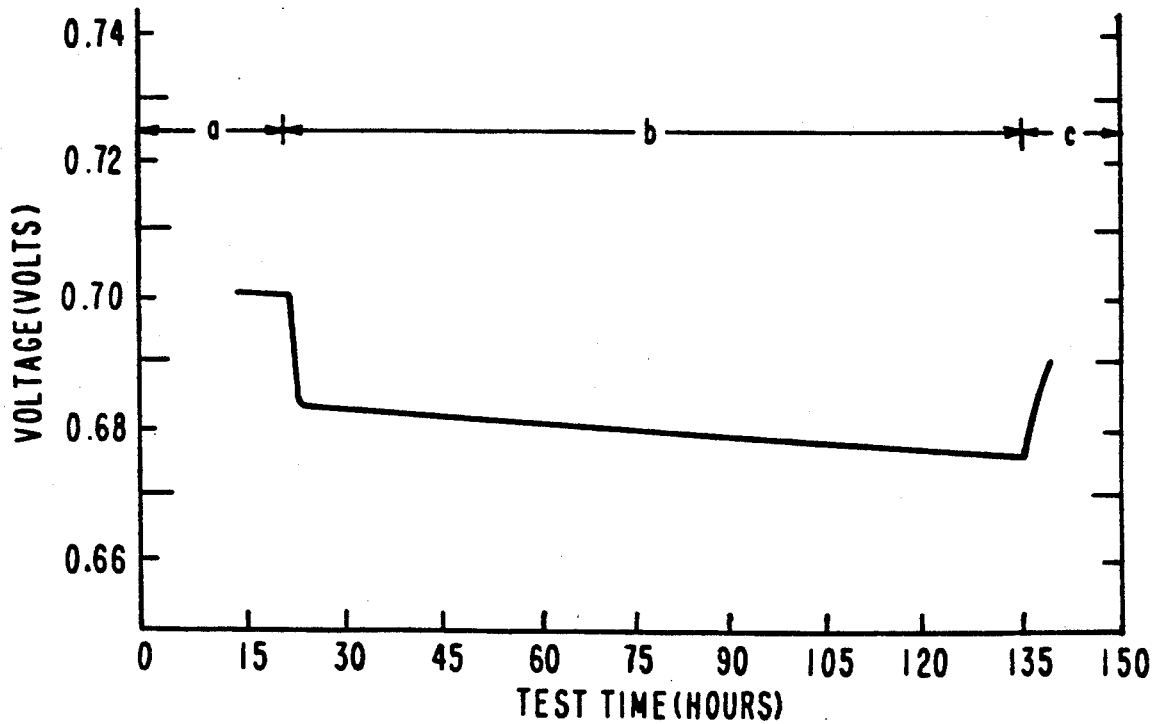
FIG. 3 is a curve of cell voltage in volts vs. time in hours for a cell prepared and operated as described in the Example, according to this invention.

FIG. 3 of the drawings shows voltage vs. test time behavior of a cell at 900° C., after impregnation, when the cell operated as a fuel cell. The cell had been operated for about 140 hours at 900° C. and 160 mA/cm$^2$, with about 115 hours being in a fuel gas containing 25 ppm (parts per million) $H_2S$, in 66.7% $H_2$, 22.2% CO and 11.1% $H_2O$. FIG. 3 shows operating voltage vs. time during this period. A voltage loss of less than 3.5% was observed during exposure to $H_2S$ which is much lower than observed at this $H_2S$ concentration for untreated anodes. The operating voltage of about 700 mV at 900° C. and 160 mA/cm$_2$, observed after the first 22 hours of the run before adding the $H_2S$, was also much higher than observed for similar cells with untreated anodes. Section (a) of the curve of FIG. 3 shows the period of operation with no $H_2S$; section (b) shows the period with 25 ppm $H_2S$; and section (c) shows the period, again, with no $H_2S$.

We claim:

1. A composite of an exterior porous elecrtrode bonded to a solid oxygen ion conducting electrolyte, where the electrolyte is also in contact with an interior electrode, the exterior electrode comprising coarse metal particles selected from the group consisting of nickel particles, cobalt particles, and mixtures thereof, having diameters from 3 micrometers to 35 micrometers, the improvement characterized in that the particles of the exterior electrode are coated with a separate electronically conductive, porous, multiphase layer, consisting essentially of:
 (a) fine metal particles selected from the group consisting of discrete nickel particles, discrete cobalt particles, and mixtures thereof, having diameters from 0.05 micrometer to 1.75 micrometer, and
 (b) conductive oxide, selected from the group consisting of cerium oxide, doped cerium oxide, strontium titanate, doped strontium titanate and mixtures thereof.

2. The composite of claim 1, where the fine metal particles of the exterior electrode have diameters from 0.25 micrometer to 0.75 micrometer and the coarse metal particles have diameters from 5 micrometers to 35 micrometers.

3. The composite of claim 1, where the multiphase layer of the exterior electrode is a complete covering and has a thickness of from 0.5 micrometer to 2.0 micrometers.

4. The composite of claim 1, where the dopants used with the conductive oxide in the multiphase layer of the exterior electrode are selected from the group consisting of Mg, Ca, Sr, Ba, La, Ce, Pr, Nd, Sm, Eu, Gd, Tb, Dy, Ho, Er, Tm, Yb, Y, Al, and mixtures thereof.

5. The composite of claim 1, where the conductive oxide of the exterior electrode is selected from the group consisting of cerium oxide and cerium oxide doped with a material selected from the group consisting of Mg, Ca, Sr, Ba, La, Ce, Pr, Nd, Sm, Eu, Gd, Tb, Dy, Ho, Er, Tm, Yb, Y, Al, and mixtures thereof.

6. The composite of claim 1, where the fine metal particles of the exterior electrode are nickel particles, which particles within the multiphase layer increase the number of electrochemically active sites on the electrode, the conductive oxide is selected from the group consisting of cerium oxide and cerium oxide doped with a material selected from the group consisting of Ca, Sm, and mixtures thereof, and the coarse metal particles are partly embedded in a skeletal structure comprising zirconia.

7. An electrochemical cell comprising:
 (1) an interior air electrode,
 (2) a solid electrolyte comprising stabilized zirconia contacting the air electrode,
 (3) an exterior porous fuel electrode bonded to the air electrode, the fuel electrode comprising coarse metal particles having diameters from 3 micrometers to 35 micrometers partly embedded in a skeletal structure comprising stabilized zirconia, and
 (4) a separate multiphase layer coating the exterior fuel electrode, the mutliphase layer consisting essentially of
  (a) fine metal particles selected from the group consisting of discrete, nickel particles discrete cobalt particles, and mixtures thereof, having diameters from 0.05 micrometer to 1.75 micrometer, and
  (b) conductive oxide selected from the group consisting of cerium oxide, doped cerium oxide, strontium titanate, doped strontium titanate, and mixtures thereof.

8. A method of coating a separate electronically conductive layer on an exterior, porous electrode bonded to a solid oxygen ion conducting electrolyte, where the electrolyte is also in contact with an interior electrode, comprising the steps:
 (1) applying, to the exterior porous electrode, an admixture consisting essentially of:
  (a) a first metal containing salt where the metal containing component is selected from the group consisting of nickel, cobalt, and mixtures thereof, and the salt component is selected from the group consisting of nitrate, acetate, propionate, butyrate, and mixtures thereof, and
  (b) a second metal containing salt where the metal containing component is selected from the group consisting of cerium, doped cerium, strontium-titanium, doped strontium-titanium, and mixtures thereof, and the salt component is selected from the group consisting of nitrate, acetate, propionate, butyrate, and mixtures thereof and
  (c) non-ionic surfactant, and
 (2) heating the coating admixture in an atmosphere reducing to nickel, cobalt, and their mixtures, at a temperature effective to form a separate, solid, electronically conductive, porous, multiphase layer consisting essentially of conductive oxide selected from the group consisting of cerium oxide, doped cerium oxide, strontium, titanate, doped strontium titanate, and mixtures thereof, containing therethrough fine metal particle precipitate selected from the group consisting of discrete nickel particles, discrete cobalt particles, and mixtures thereof, having diameters from 0.05 micrometer to 1.75 micrometers.

9. The method of claim 8, where the exterior porous electrode that is coated comprises coarse metal particles having diameters from 3 micrometers to 35 micrometers partly embedded in a skeletal structure comprising zirconia, and the fine metal particle precipitates formed in step (2) have diameters from 0.25 micrometers to 0.75 micrometers.

10. The method of claim 8, where dopants used with the metal of the second metal containing salt are selected from the group consisting of Mg, Ca, Sr, Ba, La, Ce, Pr, Nd, Sm, Eu, Gd, Tb, Dy, Ho, Er, Tm, Yb, Y, Al, and mixtures thereof, and where the heating in step (2) is at a rate of from 50° C./hour to 100° C./hour.

* * * * *